(12) United States Patent
Chahen et al.

(10) Patent No.: US 8,680,307 B2
(45) Date of Patent: Mar. 25, 2014

(54) COMPLEXES AND METHOD FOR SYNTHESIS OF GROUP 6 ORGANOMETALLICS GRAFTED ON ANIONS, AND USE THEREOF IN AN OLEFIN METATHESIS METHOD

(75) Inventors: Ludovic Chahen, Vienne (FR); Mikaël Berthod, Lyons (FR); Vinciane Kelsen, Meximieux (FR); Yves Chauvin, Tours (FR); Helene Olivier-Bourbigou, Saint Genis-Laval (FR); Christophe Vallee, Sassenage (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 608 days.

(21) Appl. No.: 12/912,032

(22) Filed: Oct. 26, 2010

(65) Prior Publication Data
US 2011/0098497 A1 Apr. 28, 2011

(30) Foreign Application Priority Data

Oct. 27, 2009 (FR) ...................................... 09 05158

(51) Int. Cl.
*C07F 5/02* (2006.01)
(52) U.S. Cl.
USPC ............................................................ 556/7
(58) Field of Classification Search
None
See application file for complete search history.

(56) References Cited

U.S. PATENT DOCUMENTS

2008/0119678 A1* 5/2008 Hock et al. .................... 585/500
2010/0168352 A1* 7/2010 Arriola et al. ................. 526/171

OTHER PUBLICATIONS

Cole, S., et al. "Transition-metal imido-boroxide complexes: a structural and spectroscopic investigation of the influence of boron," J. Chem. Soc., Dalton Trans., (2002) 4168-4174.*
Institut National de la Propriete Industrielle. "Preliminary Search Report." FR0905158. Applicant: IFP, Mailed: Apr. 30, 2010.
Schrock RR. "Olefin Metathesis by Molybendum Imido Alkylidene Catalysts." (Tetrahedron), Jul. 2, 1999, pp. 8141-8153, vol. 55, No. 27.
Jiang A J et al. "Cationic molybendum imido alkylidene complexes." (Organometallics), Sep. 8, 2008, pp. 4428-4438, vol. 27, No. 17.
Pederson, Steven F. and Richard R. Schrock. Preparation of tungsten (VI) phenylimido alkyl and alkylidene complexes. (Journal of American Chemical Society), Mar. 5, 1982, pp. 7483-7491, vol. 104, No. 26.

* cited by examiner

*Primary Examiner* — Sudhakar Katakam
(74) *Attorney, Agent, or Firm* — Millen, White, Zelano & Branigan, P.C.

(57) ABSTRACT

Novel group 6 organometallic compounds, supported on anions by means of at least one covalent metal-oxygen bond, are obtained by reaction of at least one borate or aluminate comprising at least one hydroxy group with at least one compound of a group 6 transition metal. These compounds are used in a catalytic composition utilized in an olefin metathesis method.

29 Claims, No Drawings

COMPLEXES AND METHOD FOR SYNTHESIS OF GROUP 6 ORGANOMETALLICS GRAFTED ON ANIONS, AND USE THEREOF IN AN OLEFIN METATHESIS METHOD

FIELD OF THE INVENTION

The present invention relates to novel group 6 organometallic complexes supported on anions by means of at least one covalent metal-oxygen bond. It also relates to a method for synthesizing these compounds. It also describes an olefin metathesis method using a catalytic composition utilizing the organometallic complexes according to the present invention.

BACKGROUND OF THE INVENTION

Homogeneous reactions catalysed by transition metals, allowing formation of carbon-carbon bonds, are considered to be important synthetic methods. One example thereof is the olefin metathesis reaction, which has proved its efficiency in the synthesis of high-molecular-weight polymers as well as the synthesis of medicines or other materials. Metal alkylidene complexes, notably molybdenum complexes, have shown good activities in homogeneous olefin metathesis reactions, even in the presence of various functional groups, and these performances greatly depend on the other ligands present around the metal. By way of example, R. R. Schrock's work can be mentioned, who compared the activities of many molybdenum and tungsten imidocarb complexes for the homometathesis of 1-octene (*Organometallics,* 2009, 28 (1), 355-360).

Despite these advantages, these catalysts are likely to deactivate by interaction of the organometallic species in solution, via polynuclear species formation or dismutation mechanisms. These interactions are favoured by the absence of repulsion between the metal centers, as described by R. R. Schrock for tungsten complexes (*Chem. Rev.,* 2009, 109, 3211-3226). Besides, recycling homogeneous catalysts and/or separating them from the reaction products are generally delicate aspects of homogenous processes.

Surface organometallic chemistry has been developed to overcome these drawbacks, Homogeneous catalysts grafted on an oxide surface are recyclable and the metal centers anchored to the surface are not likely to interact with one another. However, this methodology suffers from the heterogeneity of the surface sites of a solid, which leads to a multiplicity of active sites. It is furthermore difficult to control the metal content of the solid obtained or to modify the environment of the metal so as to vary its catalysis properties.

We have discovered that grafting organometallic compounds on an anion by means of at least one covalent metal-oxygen bond allows to overcome these limitations. The species formed thus has an anionic character, which affords several advantages:

- the interactions between metal centers in solution are thus reduced, due to the repulsion of the charges, and
- the entity formed is soluble in ionic solvents, which opens up the possibility of its immobilization and recycling in a two-phase technology.

DETAILED DESCRIPTION

The present invention describes group 6 organometallic compounds, supported on anions by means of at least one covalent metal-oxygen bond, of general formula I, II or III:

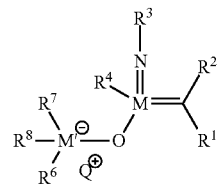

I

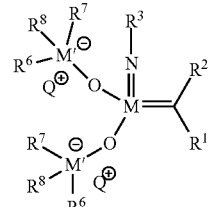

II

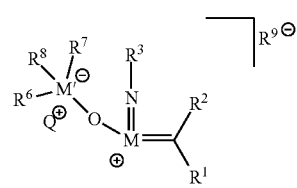

III wherein:
M represents molybdenum, tungsten,
M' represents boron or aluminium,
$R^1$, $R^2$, $R^3$ and $R^4$, identical or different, represent hydrogen, halogenides or organic radicals having 1 to 30 carbon atoms,
$R^6$, $R^7$ and $R^8$, identical or different, represent organic radicals having 1 to 30 carbon atoms,
$R^9$ represents an anion,
and $Q^+$ represents an organic or inorganic cation.

These products are obtained by reaction of at least one borate or aluminate type compound comprising at least one hydroxy group with at least one group 6 transition metal compound of imido alkylidene type.

In the aforementioned compounds, groups $R^1$, $R^2$, $R^3$ and $R^4$ represent alkyl, cycloalkyl or aryl groups, optionally substituted, cyclopentadienyls, substituted or not, alkoxy, aryloxy, amidide, hydrido, carboxylate, oxalate, β-diketiminate, iminopyrrolide, amidinate groups, and groups $R^6$, $R^7$, $R^8$, identical or different, represent alkyl radicals comprising 1 to 30 carbon atoms, saturated or unsaturated, cycloalkyl or aromatic, aryl or aralkyl radicals, optionally substituted, hydrocarbyl radicals wherein one or more hydrogen atoms are replaced by halogenides or groups comprising at least one heteroelement selected from the elements oxygen, nitrogen, sulfur or silicon, alkoxy, aryloxy or amidide groups.

The $Q^+$ cation is preferably an organic cation. It is preferably selected from the group made up of phosphonium, ammonium, guanidinium and/or sulfonium.

In the formulas hereafter, $X^1$, $X^2$, $X^3$, $X^4$, $X^5$ and $X^6$ represent hydrogen, preferably a single substituent representing hydrogen, or hydrocarbyl radicals having 1 to 30 carbon atoms, for example alkyl groups, saturated or unsaturated, cycloalkyl or aromatic, aryl or aralkyl groups, optionally substituted.

More preferably, $X^1$, $X^2$, $X^3$, $X^4$, $X^5$ and $X^6$ represent hydrocarbyl radicals having 1 to 30 carbon atoms, for example alkyl groups, saturated or unsaturated, cycloalkyl or aromatic, aryl or aralkyl groups, optionally substituted.

The sulfonium and guanidinium cations preferably meet one of the general formulas $SX^1X^2X^{3+}$ or $C(NX^1X^2)(NX^3X^4)(NX^5X^6)^+$ where $X^1$, $X^2$, $X^3$, $X^4$, $X^5$ and $X^6$, identical or different, are defined as above.

The quaternary ammonium and/or phosphonium $Q^+$ cations preferably meet one of the general formulas $NX^1X^2X^3X^{4+}$ and $PX^1X^2X^3X^{4+}$, or one of the general formulas $X^1X^2N=CX^3X^{4+}$, $X^1X^2X^3P=N=PX^5X^6X^7$ and $X^1X^2P=CX^3X^{4+}$ wherein $X^1$, $X^2$, $X^3$, $X^4$, $X^5$, $X^6$ and $X^7$, identical or different, are defined as above, The ammonium and/or phosphonium cations can also be derived from nitrogen-containing and/or phosphorus-containing heterocycles comprising 1, 2 or 3 nitrogen and/or phosphorus atoms, of general formulas:

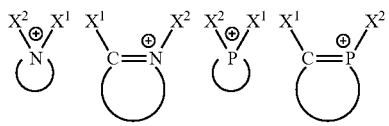

wherein the rings consist of 4 to 10 atoms, preferably 5 to 6 atoms, and $X^1$ and $X^2$, identical or different, are defined as above.

The quaternary ammonium or phosphonium cation can also meet one of the general formulas $X^1X^{2+}N=CX^3—X^7—X^3C=N^+X^1X^2$ and $X^1X^2+P=CX^3—X^7—X^3C=P+X^1X^2$ wherein $X^1$, $X^2$ and $X^3$, identical or different, are defined as above, and $X^7$ represents an alkylene or phenylene radical.

Examples of radicals from groups $X^1$, $X^2$, $X^3$, $X^4$ are the methyl, ethyl, propyl, isopropyl, primary butyl, secondary butyl, tertiary butyl, butyl, amyl, phenyl or benzyl radicals; $X^7$ can be a methylene, ethylene, propylene or phenylene group.

The present invention also describes a mixture of group 6 organometallic compounds, supported on anions by means of at least one covalent metal-oxygen bond, obtained by reaction between at least one compound A of borate or aluminate type comprising at least one hydroxy group, and at least one compound of a group 6 transition metal of imido alkylidene type, optionally in the presence of a solvent.

The present invention describes a method for synthesis of group 6 organometallic compounds supported on anions by means of at least one covalent metal-oxygen bond, obtained by reacting at least one compound A of borate or aluminate type comprising at least one hydroxy group with at least one compound of a group 6 transition metal of imido alkylidene type, optionally in the presence of a solvent.

The present invention also describes a catalytic composition resulting from contacting:
  at least one borate or aluminate type compound comprising at least one hydroxy group of general formula A,
  at least one compound of a group 6 transition metal of imido alkylidene type of formula B or B',
  and optionally a solvent.

The present invention also describes a catalytic composition comprising;
  at least one group 6 organometallic compound of general formula I, II or III, supported on anions by means of at least one covalent metal-oxygen bond,
  and optionally a solvent.

The present invention also describes an olefin metathesis method using said catalytic compositions.

The presence of the covalent metal-oxygen bond is highlighted in the present invention by the spectroscopy analysis techniques commonly known and used by the person skilled in the art (proton, carbon, fluorine and boron NMR, mass spectrometry and IR spectroscopy).

Compound A

According to the present invention, the borate or aluminate type compound comprising at least one hydroxy group can be described by general formula A:

wherein M' represents boron or aluminium, $Q^+$ represents an organic or inorganic cation, $R^6$, $R^7$, $R^8$, identical or different, represent hydrocarbyl radicals having 1 to 30 carbon atoms, for example alkyl groups, saturated or unsaturated, cycloalkyl or aromatic, aryl or aralkyl groups, optionally substituted.

$R^6$, $R^7$ and $R^8$, identical or different, can also represent hydrocarbyl radicals wherein one or more hydrogen atoms are replaced by halogenides or groups comprising at least one heteroelement such as oxygen, nitrogen, sulfur or silicon.

$R^6$, $R^7$ and $R^8$, identical or different, can also represent alkoxy, aryloxy or amidide groups.

Preferably, $R^6$, $R^7$ and $R^8$ represent the pentafluorophenyl or 3,5-(bistrifluoromethyl)phenyl radicals.

Examples of borate or aluminate type compounds that can be used in the present invention are butyl-3-methyl-1-imidazolium tris-pentafluorophenyl-hydroxyborate, 1-butyl-2,3-dimethylimidazolium tris-pentafluorophenyl-hydroxyborate, 1-ethyl-3-methylimidazolium tris-pentafluorophenyl-hydroxyborate, 1-butyl-3-butylimidazolium tris-pentafluorophenyl-hydroxyborate, N,N-butylmethylpyrrolidinium tris-pentafluorophenyl-hydroxyborate, tetrabutylphosphonium tris-pentafluorophenyl-hydroxyborate, tetraphenylphosphonium tris-pentafluorophenyl-hydroxyborate, butyl-3-methyl-1-imididazolium tris-pentafluorophenyl-hydroxyaluminate, butyl-3-methyl-1-imididazolium tris-phenylhydroxyborate, butyl-3-methyl-1-imididazolium tris-(3,5-bis(trifluoromethyl)phenyl)-hydroxyborate, or bis(triphenylphosphoranylidene)ammonium.

The Imido Alkylidene Type Transition Metal Compound

According to the present invention, the compound based on a group 6 transition metal is of imido alkylidene type.

In the sense of the present invention, what is referred to as an "imido alkylidene" type metal compound is a compound comprising a double bond M=N and a double bond M=C.

It can be described by one of the following general formulas:

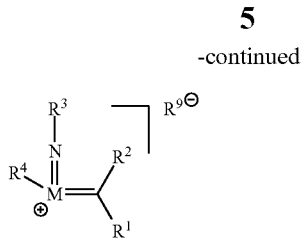

B'

In this formula, M represents molybdenum or tungsten.

$R^1$ and $R^2$, identical or different, bonded by a ring or not, represent hydrogens, halogenides (F, Cl, Br, I), alkyl, cycloalkyl or aryl groups, optionally substituted, cyclopentadienyls, substituted or not (denoted by Cp), alkoxy, aryloxy, amidide, hydrido, carboxylate, oxalate, phosphonium or siloxane groups.

$R^3$ represents alkyl, cycloalkyl or aryl groups, optionally substituted, cyclopentadienyls, substituted or not (denoted by Cp).

Preferably, $R^3$ represents the 2,6-di-isopropylephenyl or adamantyl group.

$R^4$ and $R^5$, identical or different, represent hydrogens, halogenides (F, Cl, Br, I), alkyl, cycloalkyl or aryl groups, optionally substituted, cyclopentadienyls, substituted or not (denoted by Cp), alkoxy, aryloxy, amidide, hydrido, carboxylate, oxalate, β-diketiminate, iminopyrrolide, amidinate, pyrrolide groups, optionally substituted.

$R^1$, $R^2$, $R^3$, $R^4$ and $R^5$ can be bonded to one another so as to form one or more rings.

Preferably, $R^4$ and $R^5$ are 2,2-di(trifluoromethyl)propanoxy or 2,5-dimethylpyrrolide groups.

$R^9$ represents an anion. Preferably, $R^9$ can be selected from among the following anions: halogenide, carbonate, nitrate, sulfate and hydrogenosulfate, alkylsulfate, phosphates and hydrogenophosphate, alkylphosphate, acetate, halogenoacetate, tetrafluoroborate, tetrachloroborate, hexafluorophosphate, hexafluoroantimonate, fluorosulfonate, alkylsulfonates (for example methylsulfonate), perfluoroalkylsulfonate (for example trifluoromethylsulfonate), bis(perfluoroalkylsulfonyl)amidides (for example bis trifluoromethylsulfonyl amidide of formula $N(CF_3SO_2)_2^-$), arenesulfonate, optionally substituted by halogen or halogenoalkyl groups, the tetraphenylborate anion and the tetraarylborate anions whose aromatic rings are substituted, tetra-(trifluoroacetoxy)-borate, bis-(oxalato)-borate, dicyanamide.

Preferably, $R^9$ is a $BF_4^-$, $PF_6^-$, $(B(3,5\text{-}(CF_3)_2C_6H_3)_4)^-$, $N(CF_3SO_2)_2^-$ group.

The compound of a group 6 transition metal of formula B or B' con be of higher-order monomeric, dimeric or oligomeric nature.

The adducts of the compounds of formula B or B' described above with a Lewis base can also be used according to the present invention. Examples of Lewis bases that can be used according to the present invention are ethers, amines, thioethers and phosphines.

Examples of compounds of formula B or B' of a group 6 transition metal that can be used according to the present invention are Mo(N-2,6-iPr$_2$C$_6$H$_3$)(CHCMe$_2$Ph)(2,5-MeNC$_4$H$_2$)$_2$, Mo(N-2,6-iPr$_2$C$_6$H$_3$)(CHCMe$_2$Ph)(NC$_4$H$_2$)$_2$, Mo(N-2,6-iPr$_2$C$_6$H$_3$)(CHCMe$_2$Ph)(2,5-iPrNC$_4$H$_2$)$_2$, Mo(N-2,6-iPr$_2$C$_6$H$_3$)(CHCMe$_2$Ph)(2,5-PhNC$_4$H$_2$)$_2$, Mo(N-2,6-iPr$_2$C$_6$H$_3$)(CHCMe$_3$)(2,5-MeNC$_4$H$_2$)$_2$, Mo(N-2,6-iPr$_2$C$_6$H$_3$)(CHCMe$_3$)(NC$_4$H$_2$)$_2$, Mo(N-2,6-iPr$_2$C$_6$H$_3$)(CHCMe$_3$)(2,5-PhNC$_4$H$_2$)$_2$, Mo(N-2,6-iPr$_2$C$_6$H$_3$)(CHCMe$_3$)(2,5-PhNC$_4$H$_2$)$_2$, Mo(N-2,6-Me$_2$C$_6$H$_3$)(CHCMe$_2$Ph)(2,5-MeNC$_4$H$_2$)$_2$, Mo(N-2,6-Me$_2$C$_6$H$_3$)(CHCMe$_2$Ph)(NC$_4$H$_2$)$_2$, Mo(N-2,6-Me$_2$C$_6$H$_3$)(CHCMe$_2$Ph)(2,5-iPrNC$_4$H$_2$)$_2$, Mo(N-2,6-Me$_2$C$_6$H$_3$)(CHCMe$_2$Ph)(2,5-PhNC$_4$H$_2$)$_2$, Mo(N-2,6-Cl$_2$C$_6$H$_3$)(CHCMe$_2$Ph)(2,5-MeNC$_4$H$_2$)$_2$, Mo(N-2,6-Cl$_2$C$_6$H$_3$)(CHCMe$_2$Ph)(NC$_4$H$_2$)$_2$, Mo(N-2,6-Cl$_2$C$_6$H$_3$)(CHCMe$_2$Ph)(2,5-iPrNC$_4$H$_2$)$_2$, Mo(N-2,6-Cl$_2$C$_6$H$_3$)(CHCMe$_2$Ph)(2,5-PhNC$_4$H$_2$)$_2$, Mo(N-Adamantyl)(CHCMe$_2$Ph)(2,5-MeNC$_4$H$_2$)$_2$, Mo(N-Adamantyl)(CHCMe$_2$Ph)(NC$_4$H$_2$)$_2$, Mo(N-Adamantyl)(CHCMe$_2$Ph)(2,5-iPrNC$_4$H$_2$)$_2$, Mo(N-Adamantyl)(CHCMe$_2$Ph)(2,5-PhNC$_4$H$_2$)$_2$, Mo(N-2,6-iPr$_2$C$_6$H$_3$)(CHCMe$_2$Ph)(OCMe(CF$_3$)$_2$)$_2$, Mo(N-2,6-iPr$_2$C$_6$H$_3$)(CHCMe$_2$Ph)(OC$_6$F$_5$)$_2$)$_2$, Mo(N-2,6-iPr$_2$C$_6$H$_3$)(CHCMe$_3$)(OCMe(CF$_3$)$_2$)$_2$, Mo(N-2,6-iPr$_2$C$_6$H$_3$)(CHCMe$_2$Ph)(OTf)$_2$(dme), Mo(N-2,6-iPr$_2$C$_6$H$_3$)(CHCMe$_2$Ph)Cl$_2$(dme), Mo(N-2,6-iPr$_2$C$_6$H$_3$)(CHCMe$_2$Ph)(CH$_2$-$^t$Bu)$_2$, Mo(N-2,6-iPr$_2$C$_6$H$_3$)(CHCMe$_2$Ph)(CH$_2$—CMe$_2$Ph)$_2$, W(N-2,6-iPr$_2$C$_6$H$_3$)(CHCMe$_2$Ph)(2,5-MeNC$_4$H$_2$)$_2$, W(N-2,6-iPr$_2$C$_6$H$_3$)(CHCMe$_2$Ph)(NC$_4$H$_4$)$_2$, W(N-2,6-iPr$_2$C$_6$H$_3$)(CHCMe$_3$)(OCMe(CF$_3$)$_2$)$_2$, W(N-2,6-iPr$_2$C$_6$H$_3$)(CHCMe$_2$Ph)(OC$_6$F$_5$)$_2$)$_2$, W(N-2,6-iPr$_2$C$_6$H$_3$)(CHCMe$_3$)(OCMe(CF$_3$)$_2$)(NC$_4$H$_4$).

The adducts of these compounds with Lewis bases such as ethers, amines, thioethers or phosphines can also be used according to the present invention.

Organometallic Compounds I, II or III

According to the present invention, the organometallic compounds supported on anions by means of a covalent metal-oxygen bond can be described by general formulas I, II or III, wherein M, M', $R^1$, $R^2$, $R^3$, $R^4$, $R^5$, $R^6$, $R^7$, $R^8$, $R^9$ and $Q^+$ are defined as above.

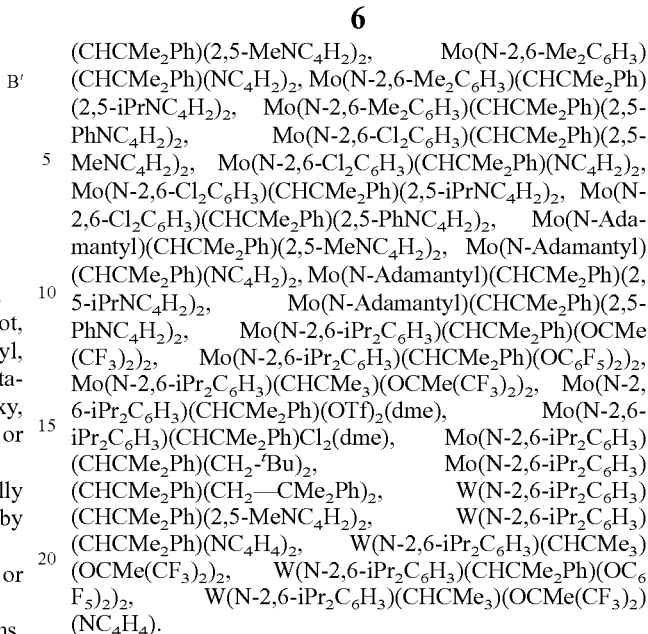

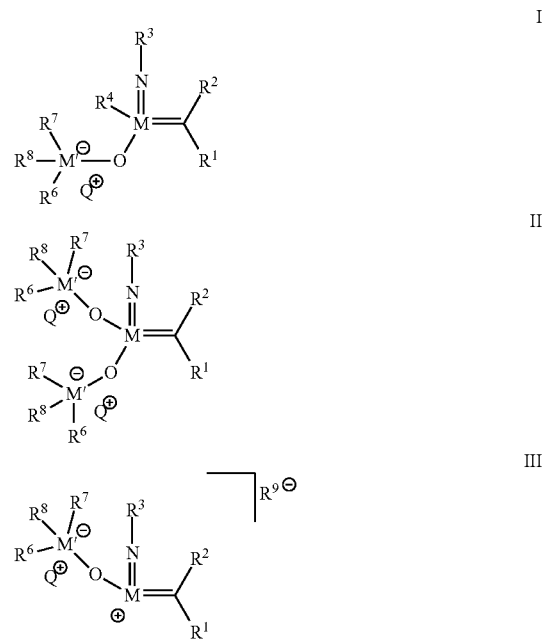

The adducts of the organometallic compounds supported on anions with a Lewis base can also be used according to the present invention.

Method of Synthesizing Organometallic Complexes I, II or III

Synthesis of the group 6 organometallic compounds supported on anions by means of at least one covalent metal-oxygen bond of general formula I, II or III is carried out through the reaction of a borate or aluminate compound comprising at least one hydroxy group (formula A) with a compound of a group 6 transition metal of imido alkylidene type (formula B or B').

The reaction can occur simply by contacting, followed by stirring, the compound of formula A with the compound of formula B or B', optionally in the presence of a solvent, Addition of the various constituents can be done in any order.

Preferably, the reaction can be carried out through addition of the compound of formula A to the compound of formula B or B' in a solvent.

The solvent can be selected from the group of organic solvents. The organic solvents are preferably aprotic solvents. Examples of solvents that can be used in the synthesis method according to the present invention are hydrocarbons such as pentane, hexane, cyclohexane or heptane, aromatic hydrocarbons such as benzene, toluene or xylenes, chlorinated solvents such as dichloromethane, or acetone, acetonitrile, diethylether, THF, DMSO and DMF.

The solvent used for the synthesis of I and II can also be an ionic liquid. The ionic liquid preferably consists of a $Q^+$ cation as defined above, associated with an organic or inorganic anion. The $Q^+$ cation is preferably an organic cation. The anion is preferably selected from among the following anions: halogenides, nitrate, sulfate, alkylsulfates, phosphate, alkylphosphates, acetate, halogenoacetates, tetrafluoroborate, tetrachloroborate, hexafluorophosphate, trifluoro-tris-(pentafluoroethyl) phosphate, hexafluoroantimonate, fluorosulfonate, alkylsulfonates (for example methylsulfonate), perfluoroalkylsulfonates (for example trifluoromethylsulfonate), bis(perfluoroalkylsulfonyl)amidides (for example bis trifluoromethylsulfonyl amidide of formula $N(CF_3SO_2)_2^-$), tris-trifluoromethylsulfonyl methylide of formula $C(CF_3SO_2)_3^-$, bis-trifluoromethylsulfonyl methylide of formula $HC(CF_3SO_2)_2^-$, arenesulfonates, optionally substituted by halogen or halogenoalkyl groups, the tetraphenylborate anion and the tetraphenylborates anions whose aromatic rings are substituted, tetra-(trifluoroacetoxy)-borate, bis-(oxalato)-borate, dicyanamide and tricyanomethylide.

A mixture of organic solvents and/or of ionic liquids can be used for the synthesis method according to the present invention.

The molar ratio of the compound of formula A to the compound of formula B or B' can range between 0.1/1 and 100/1. Preferably, the molar ratio ranges between 1/1 and 10/1, and more preferably between 1/1 and 2/1.

The temperature of the reaction between the compound of formula A and the compound of formula B or B' ranges between −100° C. and 150° C., preferably between −78° C. and 50° C.

Compounds I, II or III can be isolated by means of the conventional methods used in coordination chemistry or organic synthesis, for example precipitation or crystallization in a mixture of organic solvents.

Olefin Metathesis Method

The organometallic compounds described above are now described more precisely within the context of their use as a catalytic composition for an olefin metathesis method.

This catalytic composition comprises the following characteristic elements:
 i) at least one compound of I, II or III type,
 ii) and optionally a solvent.

The catalytic system can also be generated in situ « in situ∓ in the reactor. The catalytic composition then results from contacting the following characteristic elements:
 i) at least one compound of formula A,
 ii) at least one imido alkylidene type compound of formula B or B',
 iii) and optionally a solvent.

The olefin metathesis method according to the present invention optionally uses a solvent.

The solvent can be selected from the group of organic solvents and ionic liquids.

The organic solvent is preferably an aprotic solvent. Examples of solvents that can be used in the method of the present invention are hydrocarbons such as pentane, hexane, cyclohexane or heptane, aromatic hydrocarbons such as benzene, toluene or xylenes, chlorinated solvents such as dichloromethane, or acetone, acetonitrile, diethylether, THF, DMSO and DMF. The organic solvent is preferably a hydrocarbon or aromatic hydrocarbon solvent.

The ionic liquid preferably consists of a $Q^+$ cation as defined above, associated with an organic or inorganic anion. The $Q^+$ cation is preferably an organic cation. The anion is preferably selected from among the following anions: halogenides, nitrates, sulfates, alkylsulfates, phosphates, alkylphosphates, acetates, halogenoacetates, tetrafluoroborates, tetrachloroborates, hexafluorophosphates, trifluoro-tris-(pentafluoroethyl) phosphates, hexafluoroantimonates, fluorosulfonates, alkylsulfonates (for example methylsulfonate), perfluoroalkylsulfonates (for example trifluoromethylsulfonate), bis(perfluoroalkylsulfonyl)amidides (for example bis trifluoromethylsulfonyl amidide of formula $N(CF_3SO_2)_2^-$), tris-trifluoromethylsulfonyl methylide of formula $C(CF_3SO_2)_3^-$, bis-trifluoromethylsulfonyl methylide of formula $HC(CF_3SO_2)_2^-$, arenesulfonates, optionally substituted by halogen or halogenoalkyl groups, the tetraphenylborate anion and the tetraphenylborates anions whose aromatic rings are substituted, tetra-(trifluoroacetoxy)-borate, bis-(oxalato)-borate, dicyanamide and tricyanomethylide.

A mixture of organic solvents and/or of ionic liquids can be used in the catalytic compositions according to the present invention.

In the catalytic composition of the present invention, the molar ratio of the compound of formula A to the compound of formula B or B' ranges between 0.1/1 and 100/1, Preferably, this molar ratio ranges between 1/1 and 10/1, more preferably between 1/1 and 2/1.

The compounds that go into the catalytic composition according to the invention can be mixed in any order. Mixing can be done simply by contacting, followed by stirring, until a homogeneous liquid forms. Mixing can be achieved outside the olefin metathesis reactor or, preferably, in this reactor.

In the case of a gaseous reactant (such as ethylene for example), the reaction pressure can range between atmospheric pressure and 100 bars (10 MPa). Preferably, this pressure ranges between atmospheric pressure and 30 bars (3 MPa). This gaseous reactant can be used pure or in admixture, or diluted with a paraffin (inert).

The reactions of the method according to the invention are catalysed by the catalytic composition described above, which can be added to the reaction medium as a solid, but it can also be added in solution when it is dissolved in a solvent.

Although the method according to the present invention can be applied to any olefin metathesis reaction, it is particularly useful for olefin homometathesis and cross metathesis.

According to the invention, the olefins considered in the olefin metathesis reaction can be linear, internal or terminal. More particularly, these olefins are selected from among ethylene, propylene, n-butenes and n-pentenes, n-hexenes, n-heptenes, n-octenes, n-nonenes or n-decenes, as found in «cuts» from oil refining processes, such as the Fischer-Tropsch process, or catalytic cracking or steam cracking.

According to the invention, the olefins considered in the olefin metathesis reaction can be functionalized. Preferably, the functionalized olefins are selected from any unsaturated fatty substance comprising at least one ethylenic insaturation, acrylonitrile, acrylic acid, methyl acrylate, but-3-enenitrile, but-3-enoic acid, methyl but-3-enoate.

The olefin metathesis reaction can be carried out in a closed system, a semi-open system or under continuous conditions, with one or more reaction stages. Vigorous stirring will provide good contact between the reactant(s) and the catalytic composition.

The reaction temperature can range between −40° C. and +250° C., preferably between 0° C. and +150° C.

The following examples illustrate the invention without limiting the scope thereof.

ABBREVIATIONS USED IN THE EXAMPLES

BMI$^+$ or BMIM$^+$: 1-butyl-3-methylimidazolium
BMMI$^+$ or BMMIM$^+$: 1-butyl-2,3-dimethylimidazolium
EMI$^+$ or EMIM$^+$: 1-ethyl-3-methylimidazolium
BBI$^+$ or BBIM$^+$: 1-butyl-3-butylimidazolium
BMpy$^+$: N,N-butylmethylpyrrolidinium
Bu$_4$P$^+$: tetrabutylphosphonium
Ph$_4$P$^+$: tetraphenylphosphonium
Cp*: pentamethylcyclopentadienyl
Cp: cyclopentadienyl
NTf$_2^-$: bis trifluoromethylsulfonyl amidide of formula N(CF$_3$SO$_2$)$_2^-$
PPN$^+$: bis(triphenylphosphoranylidene)ammonium

EXAMPLES

In the following examples, the conversion corresponds to the difference between the amount of material of the limiting reactant at the beginning of the reaction and the amount of material of the limiting reactant remaining at the end of the reaction, divided by the amount of material of the limiting reactant at the beginning of the reaction. This result is multiplied by one hundred so as to obtain a conversion in percentage.

Conversion (%)=100*($n$(limiting reactant at $t_{initial}$)−$n$(limiting reactant at $t_{final}$))/$n$(limiting reactant at $t_{initial}$)

The selectivity, expressed in percentage, gives the amount of desired product formed in relation to the number of moles consumed of the limiting reactant.

Selectivity (%)=$n$(desired product)/($n$(limiting reactant at $t_{initial}$)−$n$(limiting reactant at $t_{final}$))

Examples of Preparation of Compounds of Formula A

Example 1

Preparation of (BMIM)$^+$(B(C$_6$F$_5$)$_3$OH)$^-$

A solution of 1-butyl-3-methyl imidazolium chloride (80 mg, 0.46 mmol, 1 eq) in dichloromethane (7 ml) is added dropwise to a solution of B(C$_6$F$_5$)$_3$ (234 mg, 0.46 mmol, 1 eq) in dichloromethane (7 ml), then the mixture is left under magnetic stirring for 12 h at ambient temperature. It is then added to an anhydrous lithium hydroxide suspension (13 mg, 0.55 mmol, 1.2 eq) in dichloromethane (4 ml) at ambient temperature, After 12-h stirring, the LiCl precipitate is filtered and the solvent evaporated. The tri-pentafluorophenyl-hydroxy-borate imidazolium salt thus obtained is used in the next synthesis stages. It is characterized by fluorine, proton, carbon and boron NMR, mass spectrometry and IR spectroscopy. The boron NMR chemical shift of −4.69 ppm, characteristic of the borate anion, can be observed in particular.

NMR in C$_6$D$_6$
NMR $^{19}$F (282.4 MHz, C$_6$D$_6$) (δ, ppm): −135.9 (d, 6F, $^3J_{FF}$=21.3 Hz, o-F); −161.7 (t, 3F, $^3J_{FF}$=20.7 Hz, p-F); −165.8 (m, 6F, m-F).
NMR $^1$H (300.1 MHz, C$_6$D$_6$) (δ, ppm): 0.64 (t, 3H, $^3J_{HH}$=7.4 Hz, CH$_3$); 0.75 (sext, 2H, $^3J_{HH}$=7.4 Hz, CH$_2$); 0.94 (quint, 2H, $^3J_{HH}$=7.4 Hz, CH$_2$); 2.09 (s, 1H, OH); 2.56 (s, 3H, CH$_3$); 3.04 (t, 2H, $^3J_{HH}$=7.4 Hz, CH$_2$); 5.32 (m, 1H, CH); 5.43 (m, 1H, CH); 9.19 (s, 1H, CH).
NMR $^{13}$C (75.5 MHz, C$_6$D$_6$) (δ, ppm): 13.07 (CH$_3$); 19.30 (CH$_2$); 31.63 (CH$_2$); 34.72 (CH$_3$); 49.08 (CH$_2$); 120.42 (CH (BMIM$^+$)); 121.84 (CH(BMIM$^+$)); 135.72 (CH (BMIM$^+$)); 137.57, 137.87, 139.11, 140.90, 147.25, 150.39 (CF).
NMR in CD$_2$Cl$_2$
NMR $^{19}$F (282.4 MHz, CD$_2$Cl$_2$) (δ, ppm): −137.0 (d, 6F, $^3J_{FF}$=21.3 Hz, o-F); −163.1 (t, 3F, $^3J_{FF}$=20.7 Hz, p-F); −167.0 (m, 6F, m-F).
NMR $^1$H (300.1 MHz, CD$_2$Cl$_2$) (δ, ppm): 0.92 (t, 3H, $^3J_{HH}$=7.4 Hz, CH$_3$); 1.29 (sext, 2H, $^3J_{HH}$=7.4 Hz, CH$_2$); 1.78 (quint, 2H, $^3J_{HH}$=7.4 Hz, CH$_2$); 1.84 (s, 1H, OH); 3.84 (s, 3H, CH$_3$); 4.07 (t, 2H, $^3J_{HH}$=7.4 Hz, CH$_2$); 7.21 (m, 2H, CH); 9.45 (s, 1H, CH).
NMR $^{13}$C (75.5 MHz, CD$_2$Cl$_2$) (δ, ppm): 13.32 (CH$_3$); 19.71 (CH$_2$); 32.29 (CH$_2$); 36.65 (CH$_3$); 50.47 (CH$_2$); 122.60 (CH (BMIM$^+$)); 123.89 (CH (BMIM$^+$)); 135.49 (CF); 136.97 (CH (BMIM$^+$)); 137.27, 138.69, 140.47, 146.73, 149.86 (CF).
NMR $^{11}$B (96.3 MHz, (CH$_2$Cl$_2$, 10% CD$_2$Cl$_2$)) (δ, ppm): −4.69 (s).
SM-ESI: ESI(+)=139, BMIM$^+$), (M=806, (2×BMIM$^+$+B(C$_6$F$_5$)$_3$OH$^-$)$^+$); ESI(−)(M=529, B(C$_6$F$_5$)$_3$OH$^-$), (M=1196, (2×B(C$_6$F$_5$)$_3$OH$^-$+BMIM$^+$)$^-$).
IR (KBr): ν(OH)=3679 cm$^{-1}$.

Example 2

Preparation of (Q)$^+$(B(C$_6$F$_5$)$_3$OH)$^-$: tri-pentafluorophenyl-hydroxy-borate anions The tri-pentafluorophenyl-hydroxy-borate salts associated with the various Q$^+$ cations imidazolium, pyrrolidinium or phosphonium are prepared with quantitative yields according to the same method as described in Example 1 for the 1-butyl-3-methyl imidazolim tri-pentafluorophenyl-hydroxy-borate salt.

These compounds are characterized by fluorine, proton, carbon and boron NMR, mass spectrometry and IR spectroscopy.

Q$^+$=imidazolium: cas de (BMMIM$^+$); (EMIM$^+$); (BBIM$^+$):
Characterization of (BMMIM$^+$(B(C$_6$F$_5$)$_3$OH$^-$): Colourless liquid.
NMR $^{19}$F (282.4 MHz, CD$_2$Cl$_2$) (δ, ppm): −136.8 (d, 6F, $^3J_{FF}$=21.5 Hz, o-F); −163.7 (t, 3F, $^3J_{FF}$=20.3 Hz, p-F); −167.4 (m, 6F, m-F).
NMR $^1$H (300.1 MHz, CD$_2$Cl$_2$) (δ, ppm): 0.95 (t, 3H, $^3J_{HH}$=7.4 Hz, CH$_3$); 1.35 (sext, 2H, $^3J_{HH}$=7.4 Hz, CH$_2$); 1.67 (s, 1H, OH); 1.75 (quint, 2H, $^3J_{HH}$=7.4 Hz, CH$_2$); 2.58 (s, 3H, CH$_3$); 3.78 (s, 3H, CH$_3$); 4.03 (t, 2H, $^3J_{HH}$=7.4 Hz, CH$_2$); 7.21 (d, 1H, $^3J_{HH}$=2.1 Hz, CH); 7.27 (d, 1H, $^3J_{HH}$=2.1 Hz, CH).

NMR $^{13}$C (75.5 MHz, CD$_2$Cl$_2$) (δ, ppm): 9.86 (CH$_3$); 13.41 (CH$_3$); 19.88 (CH$_2$); 31.98 (CH$_2$); 35.76 (CH$_3$); 49.24 (CH$_2$); 121.53 (CH(BMMIM$^+$)); 123.14 (CH(BMMIM$^+$)); 135.32, 137.24, 138.63, 140.48 (CF); 143.80 (C(CH$_3$) (BMMIM$^+$)); 146.80, 149.96 (CF).

NMR $^{11}$B (96.3 MHz, (CH$_2$Cl$_2$, 10% CD$_2$Cl$_2$)) (δ, ppm): −4.52 (s).

SM-ESI ESI(+) (M=153, BMMIM$^+$); ESI(−) (M=529, B(C$_6$F$_5$)$_3$OH$^−$).

IR (KBr): ν(OH)=3689 cm$^{-1}$.

Characterization of (EMIM$^+$)(B(C$_6$F$_5$)$_3$OH$^−$) Colourless liquid.

NMR $^{19}$F (282.4 MHz, CD$_2$Cl$_2$) (δ, ppm): −136.7 (d, 6F, $^3J_{FF}$=22.1 Hz, o-F); −163.0 (t, 3F, $^3J_{FF}$20.1 Hz, p-F); −167.0 (m, 6F, m-F).

NMR $^1$H (300.1 MHz, CD$_2$Cl$_2$) (δ, ppm): 1.48 (t, 3H, $^3J_{HH}$=7.4 Hz, CH$_3$); 1.90 (s, 1H, OH); 3.86 (s, 3H, CH$_3$); 4.16 (quart, 2H, $^3J_{HH}$=7.4 Hz, CH$_2$); 7.21 (m, 1H, CH); 7.25 (m, 1H, CH); 9.46 (s, 1H, CH).

NMR $^{13}$C (75.5 MHz, CD$_2$Cl$_2$) (δ, ppm): 15.32 (CH$_3$); 36.57 (CH$_3$); 45.82 (CH$_2$); 122.13 (CH(EMIM$^+$)); 123.91 (CH(EMIM$^+$)); 135.35 (CF); 137.0 (CH(EMIM$^+$)); 137.20, 138.63, 140.47, 146.72, 149.88 (CF).

NMR $^{11}$B (96.3 MHz, (CH$_2$Cl$_2$, 10% CD$_2$Cl$_2$)) (δ, ppm): −4.45 (s).

SM-ESI: ESI(+) (M=751, (2×EMIM$^+$+B(C$_6$F$_5$)$_3$OH$^−$)$^+$); ESI(−)(M=529, B(C$_6$F$_5$)$_3$OH$^−$), (M=1169, (2×B(C$_6$F$_5$)$_3$OH$^−$+EMIM$^+$)$^−$).

IR (KBr): ν(OH)=3685 cm$^{-1}$.

Characterization of (BBIM$^+$)(B(C$_6$F$_5$)$_3$OH$^−$) Colourless liquid.

NMR $^{19}$F (282.4 MHz, CD$_2$Cl$_2$) (δ, ppm): −136.8 (d, 6F, $^3J_{FF}$=21.8 Hz, o-F); −163.2 (t, 3F, $^3J_{FF}$20.3 Hz, p-F); −167.1 (m, 6F, m-F).

NMR $^1$H (300.1 MHz, CD$_2$Cl$_2$) (δ, ppm): 0.93 (t, 6H, $^3J_{HH}$=7.5 Hz, CH$_3$); 1.29 (sext, 4H, $^3J_{HH}$=7.5 Hz, CH$_2$); 1.77 (quint, 4H, $^3J_{HH}$=7.5 Hz, CH$_2$); 1.81 (s, 1H, OH); 4.09 (t, 4H, $^3J_{HH}$=7.5 Hz, CH$_2$); 7.23 (bs, 1H, CH); 7.24 (bs, 1H, CH); 9.47 (s, 1H, CH).

NMR $^{13}$C (75.5 MHz, CD$_2$Cl$_2$) (δ, ppm): 13.35 (CH$_3$); 19.75 (CH$_2$); 32.34 (CH$_2$); 50.35 (CH$_2$); 122.52 (CH(BBIM$^+$)); 135.38 (CF); 136.63 (CH(BBIM$^+$)); 137.17, 138.64, 140.43, 146.72, 149.98 (CF).

NMR $^{11}$B (96.3 MHz, (CH$_2$Cl$_2$, 10% CD$_2$Cl$_2$)) (δ, ppm): −4.43 (s).

SM-ESI: (M=181, BBIM$^+$), (M=891, (2×BBIM$^+$+B(C$_6$F$_5$)$_3$OH$^−$)$^+$); ESI(−) (M=529, B(C$_5$F$_5$)$_3$OH$^−$), (M=1239, (2×B(C$_6$F$_5$)$_3$OH$^−$+BBIM$^+$)$^−$).

IR (KBr): ν(OH)=3683 cm$^{-1}$.

Q$^+$=pyrrolidinium: case of (BMpy$^+$)

Characterization of (BMpy$^+$)(B(C$_6$F$_5$)$_3$OH$^−$): Colourless liquid.

NMR $^{19}$F (282.4 MHz, CD$_2$Cl$_2$) (δ, ppm): −136.8 (d, 6F, $^3J_{FF}$=21.9 Hz, o-F); −163.5 (t, 3F, $^3J_{FF}$=20.0 Hz, p-F); −167.2 (m, 6F, m-F).

NMR $^1$H (300.1 MHz, CD$_2$Cl$_2$) (δ, ppm): 0.98 (t, 3H, $^3J_{HH}$=7.7 Hz, CH$_3$); 1.38 (sext, 2H, $^3J_{HH}$=7.7 Hz, CH$_2$); 1.68 (s, 1H, OH); 1.70 (quint, 2H, $^3J_{HH}$=7.7 Hz, CH$_2$); 2.23 (bs, 4H, CH$_2$); 3.0 (s, 3H, CH$_3$); 3.25 (m, 2H, CH$_2$); 3.44 (m, 4H, CH$_2$).

NMR $^{13}$C (75.5 MHz, CD$_2$Cl$_2$) (δ, ppm): 13.53 (CH$_3$); 20.02 (CH$_2$); 22.05 (CH$_2$); 26.16 (CH$_2$); 49.19 (CH$_3$); 65.29 (CH$_2$); 65.38 (CH$_2$); 135.27, 137.22, 138.63, 140.40, 146.76, 149.94 (CF). RMN $^{11}$B (96.3 MHz, (CH$_2$Cl$_2$, 10% CD$_2$Cl$_2$)) (δ, ppm): −4.44 (s), SM-ESI:
ESI($^+$) (M=142, BMpy$^+$);
ESI($^-$) (M=529, B(C$_6$F$_5$)$_3$OH$^−$).

IR (KBr): ν(OH)=3688 cm$^{-1}$.

Q$^+$=phosphonium: case of (Bu$_4$P$^+$); (Ph$_4$P$^+$)

Characterization of (Bu$_4$P$^+$)(B(C$_6$F$_5$)$_3$OH$^−$: Colourless liquid.

NMR $^{19}$F (282.4 MHz, CD$_2$Cl$_2$) (δ, ppm): −136.8 (d, 6F, $^3J_{FF}$=21.7 Hz, o-F); −163.8 (t, 3F, $^3J_{FF}$=20.4 Hz, p-F); −167.3 (m, 6F, m-F).

NMR $^1$H (300.1 MHz, CD$_2$Cl$_2$) (δ, ppm): 0.96 (t, 12H, $^3J_{HH}$=6.8 Hz, CH$_3$); 1.44-1.52 (m, 16H, CH$_2$): 1.64 (s, 1H, OH); 1.97-2.07 (m, 8H, PCH$_2$).

NMR $^{13}$C (75.5 MHz, CD$_2$Cl$_2$) (δ, ppm): 13.34 (CH$_3$); 19.01 (d, $^1J_{PC}$=48.0 Hz, PCH$_2$); 23.73 (d, $^2J_{PC}$=4.6 Hz, CH$_2$); 24.22 (d, $^3J_{PC}$=15.1 Hz, CH$_2$); 135.45, 137.03, 138.71, 140.30, 146.53, 146.90 (CF), RMN $^{11}$B (96.3 MHz, CD$_2$Cl$_2$) (δ, ppm): −4.50 (s).

NMR $^{31}$P (121.5 MHz, CD$_2$Cl$_2$) (δ, ppm): 33.41 (s) ($^1J_{PC}$=47.7 Hz, $^2J_{PC}$=15.2 Hz).

SM-ESI: ESI(+) (M=259, Bu$_4$P$^+$); ESI(−) (M=529, B(C$_6$F$_5$)$_3$OH$^−$).

IR (KBr): ν(OH)=3689 cm$^{-1}$.

Characterization of (Ph$_4$P$^+$)(B(C$_6$F$_5$)$_3$OH$^−$): White foam.

NMR $^{19}$F (282.4 MHz, CD$_2$Cl$_2$) (δ, ppm): −136.6 (d, 6F, $^3J_{FF}$=21.8 Hz, o-F); −164.1 (t, 3F, $^3J_{FF}$=20.6 Hz, p-F); −167.5 (m, 6F, m-F).

NMR $^1$H (300.1 MHz, CD$_2$Cl$_2$) (δ, ppm): 1.56 (s, 1H, OH); 7.56-7.93 (m, 20H, Ph), NMR $^{13}$C (75.5 MHz, CD$_2$Cl$_2$) (δ, ppm): 117.92 (d, $^1J_{PC}$=88.9 Hz, PC); 130.89 (d, $^3J_{PC}$=12.7 Hz, m-CH); 134.74 (d, $^2J_{PC}$=10.3 Hz, o-CH); 136.01 (bs, p-CH); 135.26, 136.99, 138.35, 140.16, 146.73, 149.86 (CF).

NMR $^{11}$B (96.3 MHz, CD$_2$Cl$_2$) (δ, ppm): −4.48 (s).

NMR $^{31}$P (121.5 MHz, CD$_2$Cl$_2$) (δ, ppm): 23.43 (s) ($^1J_{PC}$=90.6 Hz, $^2J_{PC}$=11.3 Hz).

SM-ESI: ESI(+) (M=339, Ph$_4$P$^+$); ESI(−) (M=529, B(C$_6$F$_5$)$_3$OH$^−$), (M=1397, (2×B(C$_6$F$_5$)$_3$OH$^−$+Ph$_4$P$^+$)$^−$).

IR (KBr): ν(OH)=3693 cm$^{-1}$.

Q$^+$=(PPN$^+$)

A solution of (PPN)$^+$ (Cl)$^−$ (5.025 g, 8.75 mmol) in dichloromethane is added dropwise via cannula to a suspension of tris(pentafluorophenyl)borane (4.480 g, 8.75 mmol, 1 eq) in dichloromethane at ambient temperature, in an inert atmosphere. After one-night stirring, the mixture is added dropwise to a suspension of anhydrous LiOH (251 mg, 10.5 mmol, 1.2 eq) in dichloromethane at ambient temperature. After 9-day stirring, the LiCl precipitate is filtered via filter cannula and the reaction medium is evaporated under vacuum. The product is obtained in form of a white solid. Yield: 95%.

NMR $^1$H (300 MHz, CD$_2$Cl$_2$) (δ, ppm): 1.67 (s, 1H, OH); 7.40-7.55 (m, 24H, CH o, m Ph); 7.60-7.70 (m, 6H, CH p Ph).

NMR $^{11}$B (282 MHz, CD$_2$Cl$_2$) (δ, ppm): −4.10.

NMR $^{19}$F (96.3 MHz, CD$_2$Cl$_2$) (δ, ppm): −135.8 (d, 6F, $^3J_{FF}$=21.6 Hz, o-F); −163.0 (t, 3F, $^3J_{FF}$=19.6 Hz, p-F); −166.5 (m, 6F, m-F).

NMR $^{13}$C (300 MHz, CD$_2$Cl$_2$) (δ, ppm) 127.4 (dd, $^1J_{PC}$=107.9 Hz, P-C); 129.8 (m, m-CH); 132.5 (m, o-CH); 134.1 (t, $^4J_{PC}$=1.3 Hz, p-CH); 136.7 (doublet of multiplet, $^1J_{CF}$=247 Hz, C-F), 138.4 (doublet of multiplet, $^1J_{CF}$=242 Hz, C-F), 148.3 (doublet of multiplet, $^1J_{CF}$=240 Hz, C-F).

IR ν(OH)=3698 cm$^{-1}$.

AE: theoretical % C 60.75; % H 2.93; % N 1.31, experimental % C 59.58, % H 3.17, % N 1.14.

FT-MS (ESI−) m/z=528.9887 (M−)

FT-MS (ESI+): m/z=538.1849 (M+)

Example of Compounds of Formula B

The imido alkylidene type metal compounds of formula B used hereafter are:

Mo(N-2,6-iPr$_2$C$_6$H$_3$)(CHCMe$_2$Ph)(2,5-MeNC$_4$H$_2$)$_2$
Mo(N-2,6-iPr$_2$C$_6$H$_3$)(CHCMe$_2$Ph)(OCMe(CF$_3$)$_2$)$_2$.

These complexes are either commercial (Strom Chemicals) or synthesized by means of the conventional methods described in the literature (*Organometallics,* 2007, 26, 2528 et *J. Am. Chem Soc.,* 1990, 112 (10), 3875-3886).

Example of Preparation of Compounds of Type I

Example 3

Preparation of [PPM]$^+$[Mo(N-2,6-Pr$_2$C$_6$H$_3$)(CHCMe$_2$Ph)(OCMe(CF$_3$)$_2$)(OB(C$_6$F$_5$)$_3$)]$^-$ The entire experiment is carried out under an argon atmosphere. All the reactants and the solvents are first degassed and conditioned under an argon atmosphere.

122.4 mg Mo(N-2,6-iPr$_2$C$_5$H$_3$)(CHCMe$_2$Ph)(OCMe(CF$_3$)$_2$)$_2$ and 85.6 mg (PPN)$^+$(HOB(C$_6$F$_5$)$_3$))$^-$ are fed into a 30-ml Schlenk tube, provided with a magnetic stirrer, in a glove box. Stirring is achieved for 5 minutes, then 0.25 ml of the solution of complex Mo(N-2,6-Pr$_2$C$_6$H$_3$)(CHCMe$_2$Ph)(2,5-MeNC$_4$H$_2$)(OB(Mes)$_2$) (example 1) is added. The two solids are dissolved in 3 ml dichloromethane and the solution is stirred for 10 minutes at ambient temperature. The solution is then dry evaporated and 3 ml dichloromethane are added again. After 10-minute stirring, the solution is again dry evaporated and gives a golden powder. This powder is washed with 2 ml pentane. In the presence of pentane, the compound becomes oily and two phases form. The supernatant is removed via a cannula and the second phase is evaporated, which gives the product in form of a golden powder.

The isolated compound of type I (PPN)$^+$(Mo(N-2,6-Pr$_2$C$_6$H$_3$)(CHCMe$_2$Ph)(OCMe(CF$_3$)$_2$)(OB(C$_6$F$_5$)$_3$))$^-$ is characterized by fluorine, proton and boron NMR.

NMR $^{19}$F (282.4 MHz, CD$_2$Cl$_2$) (δ, ppm): −167.1 (m, 6F, o-F); −163.5 (t, 3F, $^3$J$_{FF}$=20.7 Hz, p-F); −134.0 (m, 6F, m-F); −79.0 (m, 3F, CF$_3$); −78.2 (q, 3H, $^3$J$_{FF}$=9.5 Hz, CF$_3$).

NMR $^1$H (300.1 MHz, CD$_2$Cl$_2$) (δ, ppm): 0.97 (d, 6H, $^3$J$_{HH}$=6.9 Hz, CH(CH$_3$)$_2$); 1.01 (d, 6H, $^3$J$_{HH}$=6.4 Hz, CH(CH$_3$)$_2$); 1.12 (bs, 3H, CCH$_3$(CF$_3$)$_2$); 1.43 (s, 3H, C(CH$_3$)$_2$Ph); 1.54 (s, 3H, C(CH$_3$)$_2$Ph); 3.54 (sept, 2H, $^3$J$_{HH}$=6.7 Hz, CH(CH$_3$)$_2$); 6.90-7.30 (m, 8H, Ar); 7.40-7.54 (m, 24H, Ar); 7.60-7.70 (m, 6H, Ar); 11.62 (s, 1H, =CHC(CH$_3$)$_2$).

NMR $^{11}$B (96.3 MHz, CD$_2$Cl$_2$) (δ, ppm): −0.59 (s).

Example 4

Preparation of [Ph$_4$P]$^+$[Mo(N-2,6-Pr$_2$C$_6$H$_3$)(CHCMe$_2$Ph)(OCMe(CF$_3$)$_2$)(OB(C$_6$F$_5$)$_3$)]$^-$ The entire experiment is carried out under an argon atmosphere. All the reactants and the solvents are first degassed and conditioned under an argon atmosphere.

122.4 mg Mo(N-2,6-iPr$_2$C$_5$H$_3$)(CHCMe$_2$Ph)(OCMe(CF$_3$)$_2$)$_2$ and 138.9 mg (Ph$_4$P)$^+$(HOB(C$_6$F$_5$)$_3$))$^-$ are fed into a 30-ml Schlenk tube, provided with a magnetic stirrer, in a glove box. The two solids are dissolved in 3 ml dichloromethane and the solution is stirred for 10 minutes. The solution is then dry evaporated and 3 ml dichloromethane are added again. After 10-minute stirring, the solution is again dry evaporated and gives a golden powder. This powder is washed with 2 ml pentane. In the presence of pentane, the compound becomes oily and two phases form. The supernatant is removed via a cannula and the second phase is evaporated, which gives the product in form of a golden powder.

The isolated compound of type I (Ph$_4$P)$^+$(Mo(N-2,6-Pr$_2$C$_6$H$_3$)(CHCMe$_2$Ph)(OCMe(CF$_3$)$_2$)(OB(C$_6$F$_5$)$_3$))$^-$ is characterized by fluorine, proton and boron NMR.

NMR $^{19}$F (282.4 MHz, CD$_2$Cl$_2$) (δ, ppm): −166.9 (m, OF, o-F); −163.3 (t, 3F, $^3$J$_{FF}$=20.0 Hz, p-F); −133.9 (m, 6F, m-F); −78.9 (m, 3F, CF$_3$); −78.2 (q, 3H, $^3$J$_{FF}$=9.3 Hz, CF$_3$).

NMR $^1$H (300.1 MHz, CD$_2$Cl$_2$) (δ, ppm): 0.99 (d, 6H, $^3$J$_{HH}$=6.8 Hz, CH(CH$_3$)$_2$); 1.02 (d, 6H, $^3$J$_{HH}$=7.0 Hz, CH(CH$_3$)$_2$); 1.12 (bs, 3H, CCH$_3$(CF$_3$)$_2$); 1.44 (s, 3H, C(CH$_3$)$_2$Ph); 1.56 (s, 3H, C(CH$_3$)$_2$Ph); 3.56 (sept, 2H, $^3$J$_{HH}$=6.8 Hz, CH(CH$_3$)$_2$); 6.90-7.40 (m, 8H, Ar); 7.52-7.65 (m, 8H, Ar); 7.66-7.76 (m, 8H, Ar); 7.82-7.92 (m, 4H, Ar); 11.63 (s, 1H, =CHC(CH$_3$)$_2$).

NMR $^{11}$B (96.3 MHz, CD$_2$Cl$_2$) (δ, ppm): −0.54 (s).

Example of Olefin Metathesis Catalysis

Example 5

Homometathesis of 1-octene catalysed by (PPN)$^+$(Mo(N-2,6-Pr$_2$C$_6$H$_3$)(CHCMe$_2$Ph)(OCMe(CF$_3$)$_2$)(OB(C$_6$F$_5$)$_3$))$^-$ The entire experiment is carried out under an argon atmosphere. All the reactants and the solvents are first degassed and conditioned under an argon atmosphere.

1453 mg 1-octene (Aldrich, O480-6) and 225 mg dodecane (VWR, 23,586-293 internal standard) are fed into a 50-ml Schlenk tube, provided with a magnetic stirrer. Stirring is achieved for 5 minutes, then 22 mg of complex (PPN)$^+$(Mo(N-2,6-Pr$_2$C$_6$H$_3$)(CHCMe$_2$Ph)(OCMe(CF$_3$)$_2$)(OB(C$_6$F$_5$)$_3$))$^-$ (example 3) dissolved in 1 ml dichloromethane is added. The reaction is stirred for two hours at ambient temperature and in a dark place. Analysis of the products by gas chromatography shows that tetradecene, and ethylene that is not detected, have been formed. The conversion to 1-octene is 12% and the tetradecene selectivity is 92%.

Example 6

Homometathesis of 2-pentene catalysed by (PPN)$^+$(Mo(N-2,6-Pr$_2$C$_6$H$_3$)(CHCMe$_2$Ph)(OCMe(CF$_3$)$_2$)(OB(C$_6$F$_5$)$_3$))$^-$ The entire experiment is carried out under an argon atmosphere. All the reactants and the solvents are first degassed and conditioned Under an argon atmosphere.

742 mg 2-pentene (Fluka, 14, 377-4)) and 225 mg dodecane (VWR, 23,586-293 internal standard) are fed into a 50-ml Schlenk tube, provided with a magnetic stirrer. Stirring is achieved for 5 minutes, then 22 mg of complex [PPN]$^+$[Mo(N-2,6-Pr$_2$C$_6$H$_3$)(CHCMe$_2$Ph)(OCMe(CF$_3$)$_2$)(OB(C$_6$F$_5$)$_3$)]$^-$ (example 3) dissolved in 0.5 ml dichloromethane is added. The reaction is stirred for two hours at ambient temperature and in a dark place. Analysis of the products by gas chromatography shows that 3-hexene and 2-butene have been formed. The conversion to 2-pentene is 4% and the 3-hexene selectivity is 97%.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosures of all applications, patents and publications, cited herein and of corresponding FR application No. 09/05.158, filed Oct. 27, 2009, are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A group 6 organometallic compound supported on an anion by at least one covalent metal-oxygen bond, which is one of the following formulae I, II or III:

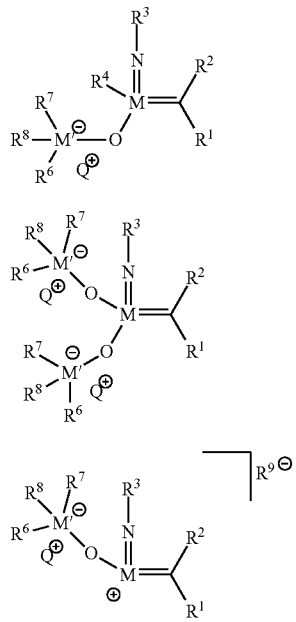

wherein:
M represents molybdenum, or tungsten,
M' represents boron or aluminium,
$R^1$, $R^2$, $R^3$ and $R^4$, identical or different, represent hydrogen, a halogenide or organic radical having 1 to 30 carbon atoms,
$R^6$, $R^7$ and $R^8$, identical or different, represent an organic radical having 1 to 30 carbon atoms,
$R^9$ represents an anion, and
$Q^+$ represents an organic or inorganic cation.

2. A compound as claimed in claim 1, wherein
$R^1$, $R^2$, $R^3$ and $R^4$ each independently represents an optionally substituted alkyl, cycloalkyl or aryl group, an optionally substituted cyclopentadienyl, or an alkoxy, aryloxy, amide, hydrido, carboxylate, oxalate, β-diketiminate, iminopyrrolide, or amidinate group, and
$R^6$, $R^7$ and $R^8$ each, identical or different, represents a saturated or unsaturated alkyl radical containing 1 to 30 carbon atoms, an optionally substituted cycloalkyl or aromatic, aryl or aralkyl radical, or a hydrocarbyl radical, wherein one or more hydrogen atoms are replaced by a halogenide or a group comprising at least one oxygen, nitrogen, sulfur or silicon, or an alkoxy, aryloxy or amide group.

3. A compound as claimed in claim 1, wherein $Q^+$ has one of the following formulas:

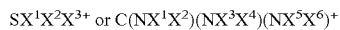

wherein $X^1$, $X^2$, $X^3$, $X^4$, $X^5$ and $X^6$ each, identical or different, represents hydrogen, or a hydrocarbyl radical having 1 to 30 carbon atoms.

4. A compound as claimed in claim 1, wherein $Q^+$ has one of the following formulas:

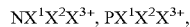

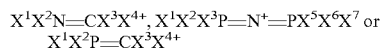

wherein $X^1$, $X^2$, $X^3$, $X^4$, $X^5$, $X^6$ and $X^7$ each, identical or different, represents hydrogen, or a hydrocarbyl radical having 1 to 30 carbon atoms.

5. A compound as claimed in claim 4, wherein $Q^+$ is derived from a compound which has one of the following formulas:

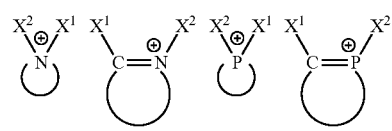

wherein the depicted rings consist of 4 to 10 atoms, and $X^1$ and $X^2$, each, identical or different, represents hydrogen, or a hydrocarbyl radical having 1 to 30 carbon atoms.

6. A mixture of group 6 organometallic compounds of imido alkylidene type, comprising at least one boron-based ligand, bonded to the metal via a covalent bond with a sulfur, oxygen or nitrogen; each supported on an anion by at least one covalent metal-oxygen bond, obtained by reaction between at least one compound of formula A and at least one compound of formula B or B', optionally in the presence of a solvent,
the compound of formula A being

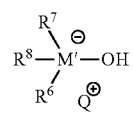

wherein M' represents boron or aluminium, $Q^+$ represents an organic or inorganic cation, $R^6$, $R^7$, and $R^8$ each, identical or different, represents an organic radical having 1 to 30 carbon atoms,
the compound of formula B or B' being

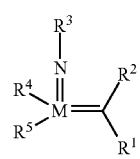

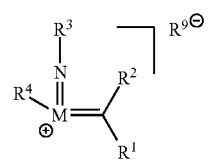

wherein M represents molybdenum or tungsten, $R^1$, $R^2$, $R^3$, $R^4$ and $R^5$ each, identical or different, represents hydrogen, a halogenide or an organic radical, and $R^9$ is an anion.

7. A mixture as claimed in claim 6, wherein the compound of formula A is butyl-3-methyl-1-imididazolium tris-pentafluorophenyl-hydroxyborate, 1-butyl-2,3-dimethylimidazolium tris-pentafluorophenyl-hydroxyborate, 1-ethyl-3-methyl-imidazolium tris-pentafluorophenyl-hydroxyborate, 1-butyl-3-butyl-imidazolium tris-penta-fluorophenyl-hydroxyborate, N,N-butylmethylpyrrolidinium tris-pentafluorophenyl-hydroxyborate, tetrabutylphosphonium tris-pentafluorophenyl-hydroxyborate, tetraphenylphosphonium tris-pentafluorophenyl-hydroxyborate, butyl-3-methyl-1-imidid-azolium tris-pentafluorophenyl-hydroxyaluminate, butyl-3-methyl-1-imididazolium tris-phenylhydroxyborate, butyl-3-methyl-1-imididazolium tris-[3,5-bis(trifluoromethyl)phenyl]-hydroxyborate, bis(triphenylphosphoranylidene)ammonium tris-pentafluorophenyl-hydroxyaluminate, or bis(triphenylphosphoranylidene)ammonium tris-pentafluorophenyl-hydroxyborate, and the compound of formula B is Mo(N-2,6-iPr$_2$C$_6$H$_3$)(CHCMe$_2$Ph)(2,5-Me$_2$NC$_4$H$_2$)$_2$, Mo(N-2,6-iPr$_2$C$_6$H$_3$)(CHCMe$_2$Ph)(NC$_4$H$_2$)$_2$, Mo(N-2,6-iPr$_2$C$_6$H$_3$)(CHCMe$_2$Ph)(2,5-iPrNC$_4$H$_2$)$_2$, Mo(N-2,6-iPr$_2$C$_6$H$_3$)(CHCMe$_2$Ph)(2,5-PhNC$_4$H$_2$)$_2$, Mo(N-2,6-iPr$_2$C$_6$H$_3$)(CHCMe$_3$) (2,5-Me$_2$NC$_4$H$_2$)$_2$, Mo(N-2,6-iPr$_2$C$_6$H$_3$)(CHCMe$_3$)(NC$_4$H$_2$)$_2$, Mo(N-2,6-iPr$_2$C$_6$H$_3$) (CHCMe$_3$)(2,5-PhNC$_4$H$_2$)$_2$, Mo(N-2,6-iPr$_2$C$_6$H$_3$)(CHCMe$_3$)(2,5-PhNC$_4$H$_2$)$_2$, Mo(N-2,6-Me$_2$C$_6$H$_3$) (CHCMe$_2$Ph)(2,5-Me$_2$NC$_4$H$_2$)$_2$, Mo(N-2,6-Me$_2$C$_6$H$_3$) (CHCMe$_2$Ph)(NC$_4$H$_2$)$_2$, Mo(N-2,6-Me$_2$C$_6$H$_3$)(CHCMe$_2$Ph)(2,5-iPrNC$_4$H$_2$)$_2$, Mo(N-2,6-Me$_2$C$_6$H$_3$)(CHCMe$_2$Ph)(2,5-PhNC$_4$H$_2$)$_2$, Mo(N-2,6-Cl$_2$C$_6$H$_3$)(CHCMe$_2$Ph)(2,5-Me$_2$NC$_4$H$_2$)$_2$, Mo(N-2,6-Cl$_2$C$_6$H$_3$)(CHCMe$_2$Ph)(NC$_4$H$_2$)$_2$, Mo(N-2,6-Cl$_2$C$_6$H$_3$)(CHCMe$_2$Ph)(2,5-iPrNC$_4$H$_2$)$_2$, Mo(N-2,6-Cl$_2$C$_6$H$_3$)(CHCMe$_2$Ph)(2,5-PhNC$_4$H$_2$)$_2$, Mo(N-Adamantyl)(CHCMe$_2$Ph)(2,5-Me$_2$NC$_4$H$_2$)$_2$, Mo(N-Adamantyl) (CHCMe$_2$Ph)(NC$_4$H$_2$)$_2$, Mo(N-Adamantyl) (CHCMe$_2$Ph)(2,5-iPrNC$_4$H$_2$)$_2$, Mo(N-Adamantyl) (CHCMe$_2$Ph)(2,5-PhNC$_4$H$_2$)$_2$, Mo(N-2,6-iPr$_2$C$_6$H$_3$)(CHCMe$_2$Ph)(OCMe(CF$_3$)$_2$)$_2$, Mo(N-2,6-iPr$_2$C$_6$H$_3$) (CHCMe$_2$Ph)(OC$_6$F$_5$)$_2$)$_2$, Mo(N-2,6-iPr$_2$C$_6$H$_3$)(CHCMe$_3$)(OCMe(CF$_3$)$_2$)$_2$, Mo(N-2,6-iPr$_2$C$_6$H$_3$)(CHCMe$_2$Ph)(OTf)$_2$(dme), Mo(N-2,6-iPr$_2$C$_6$H$_3$)(CHCMe$_2$Ph)Cl$_2$(dme), Mo(N-2,6-iPr$_2$C$_6$H$_3$)(CHCMe$_2$Ph)(CH$_2$-tBu)$_2$, Mo(N-2,6-iPr$_2$C$_6$H$_3$)(CHCMe$_2$Ph)(CH$_2$—CMe$_2$Ph)$_2$, W(N-2,6-iPr$_2$C$_6$H$_3$)(CHCMe$_2$Ph)(2,5-Me$_2$NC$_4$H$_2$)$_2$, W(N-2,6-iPr$_2$C$_6$H$_3$)(CHCMe$_2$Ph)(NC$_4$H$_4$)$_2$, W(N-2,6-iPr$_2$C$_6$H$_3$)(CHCMe$_3$) (OCMe(CF$_3$)$_2$)$_2$, W(N-2,6-iPr$_2$C$_6$H$_3$)(CHCMe$_2$Ph)(OC$_6$F$_5$)$_2$)$_2$, or W(N-2,6-iPr$_2$C$_6$H$_3$)(CHMe$_3$) (OCMe(CF$_3$)$_2$)(NC$_4$H$_4$).

8. A method for synthesis of a compound as claimed in claim 1, comprising reacting a compound of formula A with a compound of formula B or B', optionally in the presence of a solvent, wherein formula A is:

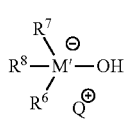

A wherein M' represents boron or aluminium, Q+represents an organic or inorganic cation, R$^6$, R$^7$, and R$^8$ each, identical or different, represents an organic radical having 1 to 30 carbon atoms, and formulas B and B' are:

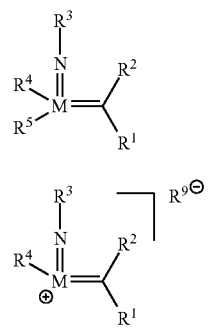

B

B' wherein M represents molybdenum or tungsten, R$^1$, R$^2$, R$^3$, R$^4$ and R$^5$ each, identical or different, represents hydrogen, an organic radical or a halogenide, and R$^9$ is an anion.

9. A method as claimed in claim 8, wherein the solvent is an organic solvent or an ionic liquid, or a mixture thereof.

10. A method as claimed in claim 8, wherein the molar ratio of the compound of formula A to the compound of formula B or B' is between 0.1/1 and 100/1.

11. A method as claimed in claim 8, wherein the reaction temperature is between −100° C. and 150° C.

12. A catalytic composition comprising:
i) at least one compound of formula I, II or III,

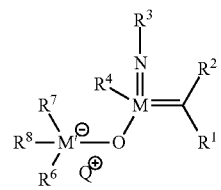

I

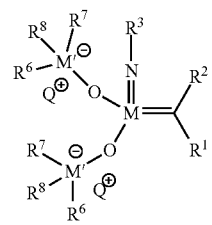

II

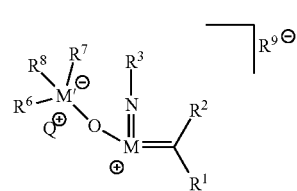

III wherein:
M represents molybdenum or tungsten,
M' represents boron or aluminium,
R$^1$, R$^2$, R$^3$ each, identical or different, represents hydrogen, a halogenide or organic radical having 1 to 30 carbon atoms, R$^6$, R$^7$, and R$^8$ each, identical or different, represents an organic radical having 1 to 30 carbon atoms,
R$^9$ represents an anion, and
Q$^+$ represents an organic or inorganic cation, and
ii) a solvent.

13. A catalytic composition according to claim 12, resulting from contacting:
i) at least one compound of formula A:

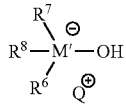

A wherein M' represents boron or aluminium, Q⁺ represents an organic or inorganic cation, $R^6$, $R^7$, and $R^8$ each, identical or different, represents an organic radical having 1 to 30 carbon atoms,
ii) at least one compound of formulas B or B':

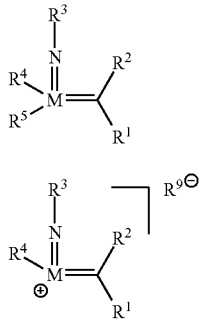

wherein M represents molybdenum or tungsten, $R^1$, $R^2$, $R^3$, $R^4$ and $R^5$ each, identical or different, represent hydrogen, or an organic radical or halogenide having 1 to 30 carbon atoms, and $R^9$ is an anion, and
iii) a solvent.

14. A catalytic composition as claimed in claim 12, wherein the solvent is an organic solvent or an ionic liquid, or a mixture thereof.

15. A catalytic composition as claimed in claim 12, wherein the molar ratio of the compound of formula A to the compound of formula B or B' is between 0.1/1 and 100/1.

16. An olefin metathesis method, comprising performing said olefin metathesis through a catalytic reaction, wherein the catalyst is a catalytic composition as claimed in claim 12.

17. A method as claimed in claim 16, wherein the reaction temperature is between −40° C. and 250° C.

18. A method as claimed in claim 16, wherein the olefin is propylene, n-butene, n-pentene, n-hexene, n-heptene, n-octene, or an alkyl oleate, or a mixture thereof in pure or diluted form, or originates from an oil refining process.

19. A compound as claimed in claim 3, wherein a single one of $X^1$, $X^2$, $X^3$, $X^4$, $X^5$ and $X^6$ represents hydrogen, and the others of $X^1$, $X^2$, $X^3$, $X^4$, $X^5$ and $X^6$ each, identical or different, represents a hydrocarbyl radical having 1 to 30 carbon atoms.

20. A compound as claimed in claim 4, wherein a single one of $X^1$, $X^2$, $X^3$, $X^4$, $X^5$, $X^6$ and $X^7$ represents hydrogen, and the others of $X^1$, $X^2$, $X^3$, $X^4$, $X^5$, $X^6$ and $X^7$ each, identical or different, represents a hydrocarbyl radical having 1 to 30 carbon atoms.

21. A compound as claimed in claim 5, wherein the depicted rings consist of to 6 atoms, and one of $X^1$ and $X^2$ represents hydrogen, and the other of $X^1$ and $X^2$ represents a hydrocarbyl radical having 1 to 30 carbon atoms.

22. A method as claimed in claim 9, wherein the solvent is an aprotic solvent or a mixture of an aprotic solvent with an ionic liquid.

23. A method as claimed in claim 10, wherein the molar ratio of the compound of formula A to the compound of formula B or B' is between 1/1 and 10/1.

24. A method as claimed in claim 11, wherein the reaction temperature is between −78° C. and 50° C.

25. A catalytic composition as claimed in claim 15, wherein the molar ratio of the compound of formula A to the compound of formula B or B' is between 1/1 and 10/1.

26. A catalytic composition as claimed in claim 15, wherein the molar ratio of the compound of formula A to the compound of formula B or B' is between 1/1 and 2/1.

27. A mixture as claimed in claim 7, wherein the compound of formula B is Mo(N-2,6-iPr₂C₆H₃)(CHCMe₂Ph)(NC₄H₂)₂, Mo(N-2,6-iPr₂C₆H₃)(CHCMe₂Ph)(2,5-iPrNC₄H₂)₂, Mo(N-2,6-iPr₂C₆H₃)(CHCMe₂Ph)(2,5-PhNC₄H₂)₂, Mo(N-2,6-iPr₂C₆H₃)(CHCMe₃)(NC₄H₂)₂, Mo(N-2,6-iPr₂C₆H₃)(CHCMe₃)(2,5-PhNC₄H₂)₂, Mo(N-2,6-iPr₂C₆H₃)(CHCMe₃)(2,5-PhNC₄H₂)₂, Mo(N-2,6-Me₂C₆H₃)(CHCMe₂Ph)(NC₄H₂)₂, Mo(N-2,6-Me₂C₆H₃)(CHCMe₂Ph)(2,5-iPrNC₄H₂)₂, Mo(N-2,6-Me₂C₆H₃)(CHCMe₂Ph)(2,5-PhNC₄H₂)₂, Mo(N-2,6-Cl₂C₆H₃)(CHCMe₂Ph)(NC₄H₂)₂, Mo(N-2,6-Cl₂C₆H₃)(CHCMe₂Ph)(2,5-iPrNC₄H₂)₂, Mo(N-2,6-Cl₂C₆H₃)(CHCMe₂Ph)(2,5-PhNC₄H₂)₂, Mo(N-Adamantyl)(CHCMe₂Ph)(NC₄H₂)₂, Mo(N-Adamantyl)(CHCMe₂Ph)(2,5-iPrNC₄H₂)₂, Mo(N-Adamantyl)(CHCMe₂Ph)(2,5-PhNC₄H₂)₂, Mo(N-2,6-iPr₂C₆H₃)(CHCMe₂Ph)(OCMe(CF₃)₂)₂, Mo(N-2,6-iPr₂C₆H₃)(CHCMe₂Ph)(OC₆F₅)₂)₂, Mo(N-2,6-iPr₂C₆H₃)(CHCMe₃)(OCMe(CF₃)₂)₂, Mo(N-2,6-iPr₂C₆H₃)(CHCMe₂Ph)(OTf)₂(dme), Mo(N-2,6-iPr₂C₆H₃)(CHCMe₂Ph)Cl₂(dme), Mo(N-2,6-iPr₂C₆H₃)(CHCMe₂Ph)(CH₂-tBu)₂, Mo(N-2,6-iPr₂C₆H₃)(CHCMe₂Ph)(CH₂—CMe₂Ph)₂, W(N-2,6-iPr₂C₆H₃)(CHCMe₂Ph)(NC₄H₄)₂, W(N-2,6-iPr₂C₆H₃)(CHCMe₃)(OCMe(CF₃)₂)₂, W(N-2,6-iPr₂C₆H₃)(CHMe₂Ph)(OC₆F₅)₂)₂, or W(N-2,6-iPr₂C₆H₃)(CHCMe₃)(OCMe(CF₃)₂)(NC₄H₄).

28. A compound as claimed in claim 1, wherein $R^9$ is selected from the group consisting of halogenide, carbonate, nitrate, sulfate, hydrogenosulfate, alkylsulfate, phosphates, hydrogenophosphate, alkylphosphate, acetate, halogenoacetate, tetrafluoroborate, tetrachloroborate, hexafluorophosphate, hexafluoroantimonate, fluorosulfonate, alkylsulfonates, methylsulfonate), perfluoroalkylsulfonate, trifluoromethylsulfonate, bis(perfluoroalkylsulfonyl)amidides, bis trifluoromethylsulfonyl amidide of formula $N(CF_3SO_2)_2^-$, arenesulfonate that is optionally substituted by one or more halogen or halogenoalkyl groups, tetraphenylborate anion, tetraarylborate anion whose aromatic rings are substituted, tetra-(trifluoroacetoxy)-borate, bis-(oxalato)-borate, and dicyanamide.

29. A compound as claimed in claim 1, wherein $R^9$ is $BF_4^-$, $PF_6^-$, $[B[3,5-(CF_3)_2C_6H_3]_4]$, or $N(CF_3SO_2)_2$.

* * * * *

UNITED STATES PATENT AND TRADEMARK OFFICE
CERTIFICATE OF CORRECTION

PATENT NO. : 8,680,307 B2  Page 1 of 1
APPLICATION NO. : 12/912032
DATED : March 25, 2014
INVENTOR(S) : Chahen et al.

It is certified that error appears in the above-identified patent and that said Letters Patent is hereby corrected as shown below:

In the Claims

Column 20, line 2 reads "depicted rings consists of to 6 atoms, and one of $X^1$ and $X^2$" should read -- depicted rings consists of 5 to 6 atoms, and one of $X^1$ and $X^2$ --

Column 20, line 60 reads "$PF_6^-$, $[B[3,5-(CF_3)_2C_6H_3]_4]$, or $N(CF_3SO_2)_2$." should read -- $PF_6^-$, $[B[3,5-(CF_3)_2C_6H_3]_4]$, or $N(CF_3SO_2)_2^-$. --

Signed and Sealed this
Twenty-third Day of September, 2014

Michelle K. Lee
*Deputy Director of the United States Patent and Trademark Office*